US006982157B1

(12) United States Patent
Pears et al.

(10) Patent No.: US 6,982,157 B1
(45) Date of Patent: Jan. 3, 2006

(54) DRUG COMBINATIONS COMPRISING (E)-7-[4-(4-FLUOROPHENYL)-6-ISOPROPYL-2-[METHYLSULFONYL)AMINO] PYRIMIDIN-5-YL] (3R,5S) -3,5-DIHYDROXYHEPT-6-ENOIC ACID AND AN INHIBITOR, INDUCER OR SUBSTRATE OF P450 ISOENZYME 3A4

(75) Inventors: John S Pears, Macclesfield (GB); Ali Raza, Wilmington, DE (US); Howard G Hutchinson, Wilmington, DE (US); Dennis Schneck, Wilmington, DE (US); Takahiko Baba, Toyonaka (JP); Akira Touchi, Toyonaka (JP)

(73) Assignees: AstraZeneca AB, London (GB); Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/889,414

(22) PCT Filed: Feb. 1, 2000

(86) PCT No.: PCT/GB00/00278

§ 371 (c)(1),
(2), (4) Date: Nov. 13, 2001

(87) PCT Pub. No.: WO00/45817

PCT Pub. Date: Aug. 10, 2000

(30) Foreign Application Priority Data

| Feb. 6, 1999 | (GB) | ................................... 9902593 |
| Sep. 8, 1999 | (GB) | ................................... 9921063 |
| Sep. 8, 1999 | (GB) | ................................... 9921064 |

(51) Int. Cl.
*C12N 9/99* (2006.01)
(52) U.S. Cl. ................................................... 435/184
(58) Field of Classification Search ............... 519/9
See application file for complete search history.

(56) References Cited

U.S. PATENT DOCUMENTS 4,895,726 A * 1/1990 Curtet et al.
6,576,660 B1 * 6/2003 Liao et al.

FOREIGN PATENT DOCUMENTS

| EP | 0 521 471 | | 1/1993 |
| EP | 0724877 | * | 8/1996 |
| JP | 401254624 | * | 10/1989 |
| JP | 405194209 | * | 8/1993 |
| WO | WO 99/22728 | * | 5/1999 |

OTHER PUBLICATIONS

Robert H. Knopp, "Drug treatment of lipid disorders", The New England Journal of Medicine, vol. 341, 1999, p. 498-511.
Kantola et al., "Effect of itraconazole on the pharmacokinetics of atorvastatin", Clinical Pharmacology & Therapeutics, vol. 64, 1998, p. 58-65.
Neuvonen et al., "Simvastatin but not pravastatin is very susceptible to interaction with the CYP3A4 inhibitor itraconazole", Clinical Pharmacology & Therapeutics, vol. 63, 1998, p. 332-341.
Neuvonen et al., "Itraconazole drstically increases plasma concentrations of lovastatin and lovastatin acid", Clinical Pharmacology & Therapeutics, vol. 60, 1996, p. 54-61.
Hunninghake, "HMG CoA reductase inhibitors", Current Opinion in Lipidology 1992; 3:22-28 (cited in the specification at p. 3, lines 11-12).
Miller et al., "Clinical Pharmacokinetics of Fibric Acid Derivatives (Fibrates)", Clin Pharmacokinet Feb 1998; 34 (2): 155-162.
Williams et al., "Pharmacokinetic-Pharmacodynamic Drug Interactions with HMG-CoA Reductase Inhibitors", Clin Pharmacokinet 2002; 41(5): 343-370.

* cited by examiner

*Primary Examiner*—Michael Meller
(74) *Attorney, Agent, or Firm*—Morgan, Lewis & Bockius LLP

(57) ABSTRACT

The invention concerns safe non-interacting drug combinations of a 3-hydroxy-3-methylglutaryl coenzyme A (HMG-CoA) reductase inhibitor, which is (E)-7-[4-(4-fluorophenyl)-6-isopropyl-2-[methyl(methylsulfonyl)amino] pyrimidin-5-yl](3R,5S)-3,5 -dihydroxyhept-6-enoic acid or a pharmaceutically acceptable salt thereof (the Agent) and a drug which is either an inducer, inhibitor or a substrate of cytochrome P450, in particular cytochrome P450 isoenzyme 3A4. Particular combinations are useful in treating hyperlipidaemia in humans who are receiving immunosuppressive chemotherapy. A preferred combination is the Agent and a fibrate drug, the use of such a combination in treating hyperlipidaemia in mammals, and medicaments containing such a combination for use in such treatments.

4 Claims, No Drawings

DRUG COMBINATIONS COMPRISING (E)-7-[4-(4-FLUOROPHENYL)-6-ISOPROPYL-2-[METHYLSULFONYL)AMINO] PYRIMIDIN-5-YL] (3R,5S) -3,5-DIHYDROXYHEPT-6-ENOIC ACID AND AN INHIBITOR, INDUCER OR SUBSTRATE OF P450 ISOENZYME 3A4

This application is the National Phase of International Application PCT/GB00/00278 filed Feb. 1, 2000 which designated the U.S. and that International Application was published under PCT Article 21(2) in English.

The invention concerns safe non-interacting drug combinations of a 3-hydroxy-3-methylglutaryl coenzyme A (HMG—CoA) reductase inhibitor, which is (E)-7-[4-(4-fluorophenyl)-6-isopropyl-2-[methyl(methylsulfonyl) amino]pyrimidin-5-yl] (3R,5S)-3,5-dihydroxyhept-6-enoic acid or a pharmaceutically acceptable salt thereof (the Agent) and a drug which is either an inducer, inhibitor or a substrate of cytochrome P450, in particular cytochrome P450 isoenzyme 3A4. Particular combinations are useful in treating hyperlipidaemia in humans who are receiving immunosuppressive chemotherapy. A preferred combination is the Agent and a fibrate drug, the use of such a combination in treating hyperlipidaemia in mammals, and medicaments containing such a combination for use in such treatments.

Hypercholesterolaemia is one of the strongest risk factors for atherosclerosis which is associated with coronary artery disease (including angina pectoris, myocardial infarction and mortality), stroke (including cerebro vascular accident and transient ischaemic attack) and peripheral arterial occlusive disease. Several types of hypercholesterolaemia exist. The magnitude of hypercholesterolaemia may have consequences for the therapy, but in general, any reduction of elevated plasma cholesterol levels is generally accepted to result in an improvement of the risk profile. Dietary improvement and increased exercise are essential first steps and should continue even if drug therapy is instituted, but the therapeutic potential of drug therapy is significantly larger. Several types of drug therapy for hypercholesterolaemia are currently available. Guidelines exist for the treatment of hypercholesterolaemia for example, American Heart Association (AHA) (Anon 1988), Updated Sheffield treatment tables (Heart (1998) 80 Supp. 2 S1–S29) and Recommendations of the task force of the European Society of Cardiology Guidelines (Pyorala 1994).

HMG-CoA reductase inhibitors are the most widely used prescription medication for the treatment of hypercholesterolaemia. By inhibiting the rate-controlling step in cholesterol biosynthesis, these agents effectively lower the plasma concentrations of atherogenic particles containing cholesterol such as low-density lipoprotein (LDL-C) and very low-density lipoprotein (VLDL-C). Partial inhibition of hepatic cholesterol synthesis causes up-regulation of hepatic membrane LDL-C receptors which are responsible for the clearance of LDL-C from the circulation. In addition, reduced hepatic synthesis of cholesterol is thought to result in a modest reduction in the secretion of VLDL-C particles by the liver. Clinical trials with certain HMG Co A-reductase inhibitors, such as in the Scandinavian Simvastatin Survival Study, confirm a reduction in cardiovascular morbidity and mortality with such agents, and may even promote regression of atherosclerotic vascular lesions. Various HMG Co A-reductase inhibitors are marketed, and are collectively referred to as 'statins'.

Despite the impressive benefits of statin therapy, less than optimal therapeutic results may be achieved in some subjects, particularly in the more severe classes of hypercholesterolaemia. This can be due to the occurrence of reversible increases in liver transaminase levels at higher dose levels of statins as well as differences in efficacy between different statins. Clinically important (>3 times upper limit of normal [ULN]) elevations in serum alanine aminotransferase [ALT]) have been reported for atorvastatin in 0.8 percent of patients at low doses of atorvastatin and higher at raised doses (European Summary of Product Characteristics [SmPC] for atorvastatin [Lipitor™]). In all cases the effect is dose-related and reversible. In general it is the incidence of ALT increases which limits dose escalation of statins rather than a limit to further increases in efficacy.

The first generation statins (such as lovastatin, pravastatin and simvastatin—prodrug derivatives of fungal metabolites—and fluvastatin) are categorised in that they achieve only a limited cholesterol lowering affect before the dose administered is limited by elevations in serum ALT. Second generation "superstatins" (such as atorvastatin—synthetic compounds—structurally distinct from first generation compounds) inhibitors are categorised in that they lower cholesterol levels to a much higher degree than the earlier first generation of statins before their dose is limited by serum ALT levels. Atorvastatin has been successful over the first generation of statins. Since its launch in the USA atorvastatin has reached sales in 1998, doubling from 1997, of $2.2 billion, capturing 38% of new prescriptions for cholesterol-lowering agents in the US and is now the most widely prescribed hypolipidaemic agent in the US (Warner-Lambert 1998 annual results).

An additional adverse event, reported for statins in general, is myopathy, defined as symptoms of muscle pain, tenderness and weakness, with creatinine kinase (CK) values>10× Upper Limit of Normal (ULN). This adverse event is not considered to be dose related, and in addition the adverse events are potentially more serious, and consequently more problematical. In severe cases this can lead to rhabdomyolysis, which is a rare life threatening condition sometimes associated with renal failure. The incidence of raised CK levels (>10×ULN–on 2 occasions at least 1 week apart with symptoms=myositis according to FDA) for statins has been reported as 3.1 percent. (SmPC for atorvastatin). Myopathy and rhabdomyolysis have been particularly associated with taking a statin in combination with gemfibrozil, niacin, cyclosporin or erythromycin, (Hunninghake H. Et al. Current Opinion in Lipidolgy (1992), 3, 22–28) which are all substrates for P450 isoenzyme 3A4. The increase in adverse events associated with taking a combination of a statin drug with one of the other drugs mentioned above is probably due to a drug:drug interaction likely related to the metabolism of most statins also by the same cytochrome P450 isoenzyme 3A4. Therefore when a drug which is also metabolised by P450 3A4 is administered alongside a statin which also is metabolised by P450 3A4, the side effects discussed above are more likely to occur. Increase in the side effects, such as muscle damage, is thought to be due to elevated statin levels in muscle cells inhibiting farnesylation and geranylgeranylation of muscle proteins. Elevated levels of statins may be caused by any drug which affects P450 3A4. Therefore, currently on the labels of all commercially available statins the use of the statin in combination with drugs that are metabolised by P450 3A4 is not recommended and is contraindicated in certain cases.

Nearly all drugs are metabolised to some degree in the human, generally to a less lipid soluble compound which is more easily excreted by the kidney or in liver bile. The liver is the major site of drug metabolism and many drug metabolising enzymes occur at high concentration in the endoplasmic reticulum (which form microsomes upon homogenisation) of liver parenchymal cells (hepatocytes). Cytochrome P450 represents a major class of drug metabolising enzymes and exists as a family of isoenzymes found in hepatic microsomes. Six specific P450 isoenzymes are responsible for the metabolism of most of the commonly used drugs, namely P450 1A2, 2C9, 2C19, 2D6, 2E1 and 3A4.

A major disadvantage of the currently available "super statin", atorvastatin, is that atorvastatin is metabolised by cytochrome P450 enzymes, in particular 3A4, which may cause drug interactions with other drugs which are inducers, inhibitors or substrates of the same P450 enzyme which metabolises atorvastatin. All of the first generation of statins are metabolised by P450 also. However, the rate of metabolism of pravastatin is sufficiently low that it is considered less susceptible to clinically relevant drug interactions. Therefore despite the lower efficacy of pravastatin, in its currently available doses, at reducing hypercholesterolaemia this is currently the statin of choice in combination with other drugs where the possibility of drug interactions is unacceptably high.

(E)-7-[4-(4-fluorophenyl)-6-isopropyl-2-[methyl(methylsulfonyl)amino]pyrimidin-5-yl] (3R,5S)-3,5-dihydroxyhept-6-enoic acid or a pharmaceutically acceptable salt thereof (the calcium salt of which is disclosed in FIG. 1 below), hereinafter referred to as the Agent, is also a statin and belongs to the class of what is now starting to be called a "superstatin".

The Agent is disclosed in European Patent Application, Publication No. 0521471, and in Bioorganic and Medicinal Chemistry, (1997), 5(2), 437–444 as an inhibitor of HMG-CoA reductase which is a major rate-limiting enzyme in cholesterol biosynthesis. The Agent is described as useful in the treatment of hypercholesterolaemia, hyperlipoproteinaemia and atherosclerosis.

The Agent is not metabolised by cytochrome P450 3A4 and therefore does not possess the same potential for drug interaction shared with the currently available "super statin", i.e. atorvastatin, or any of the other currently available statins.

Therefore we present as a feature of the invention a non-interacting drug combination comprising a HMG CoA reductase inhibitor, which is the Agent, and a drug which is an inhibitor, inducer or substrate of P450 in particular, isoenzyme 3A4.

As a further feature of the invention we present use of a HMG CoA reductase inhibitor, which is the Agent, in the preparation of a medicament for use in combination therapy with a drug which is an inhibitor, inducer or substrate of P450, in particular, isoenzyme 3A4.

As a further feature of the invention we present use of a drug which is an inhibitor, inducer or substrate of P450, in particular, isoenzyme 3A4 in the preparation of a medicament for use in combination therapy with a HMG CoA reductase inhibitor, which is the Agent.

As a further feature of the invention we present a pharmaceutical formulation comprising the Agent, a drug which is an inducer, inhibitor or substrate of P450 isoenzyme 3A4 and a pharmaceutically-acceptable diluent, carrier or adjuvant.

As a further feature of the invention we present a pharmacy pack comprising a first drug which is the Agent and a second drug which is an inducer, inhibitor or substrate of P450 isoenzyme 4A4.

By the term "inducer of P450" we mean a drug which increases the rate at which a P450 enzyme, in particular isoenzyme 3A4, metabolises a substrate, for example by increasing the activity of the P450 enzyme, decreasing the rate of biological inactivation of the P450 enzyme or by increasing the rate of transcription of the P450 gene.

By the term "inhibitor of P450" we mean a drug which lowers the rate at which a P450 enzyme, in particular isoenzyme 3A4, metabolises a substrate, for example by lowering the activity of the P450 enzyme or by lowering the rate of transcription of the P450 gene.

By the term "substrate of P450" we mean a drug which is metabolised by a P450 enzyme, in particular isoenzyme 3A4.

By the term "non-interacting drug combination" we mean a drug combination for which there is no adverse affect to the patient by its administration through the mechanism of drug metabolism by cytochrome P450 isoenzyme 3A4. It is recognised that in certain instances a drug interaction may nevertheless occur between two such drugs when in combination through a completely different mechanism not involving drug metabolism, such as affecting drug absorption.

Whether a drug is an inhibitor, inducer or substrate of a P450 enzyme can be easily determined by procedures known to the skilled person. Such procedures may involve the exposure of a radiolabelled drug to hepatocytes or hepatocyte microsomes or isolated P450 enzyme and the use of analytic techniques, such as HPLC, in determining metabolite formation. A specific procedure is described herein.

By the term "combination" we mean either that the Agent and the drug of the combination are administered together in the same pharmaceutical formulation or that the Agent and the drug are administered separately. When administered separately components of the combination may be administered to the patient simultaneously or sequentially.

We have found that the Agent is not metabolised significantly by the major cytochrome P450 isoenzymes 1A2, 2C9, 2C19, 2D6 and 3A4. This is a further feature of the invention.

Preferred non-interacting combinations of the invention include those in which the Agent is combined with a drug which is also involved in lowering cholesterol and is also an inducer, inhibitor or substrate of P450 3A4. Examples include fibrates, such as bezafibrate, clofibrate, ciprofibrate, fenofibrate and gemfibrizol (preferably fenofibrate), and niacin. Specific embodiments of this preferred feature are described in Section B below.

Preferred non-interacting combinations of the invention include those in which the Agent is combined with a drug which is involved in treating cardiovascular conditions and which is also an inhibitor, inducer or substrate of P450 3A4. Examples include digitoxin, diltiazem, losartan, nifedipine, quinidine, verapamil and warfarin.

Preferred non-interacting combinations of the invention include those in which the Agent is combined with cyclosporin and/or tacrolimus (FK506) and therefore has utility in treating elevated cholesterol levels in patients who are about to, or have recently undergone, a transplantation operation. Specific embodiments of this preferred feature are described below.

Preferred patients in which the combination of the invention is to be administered are those who suffer from myopathy or rhabdomylosis or who have already been found to suffer from myopathy or rhabdomylosis when treated with HMG Co A reductase inhibitor which is metabolised by P450 3A4, for example atorvastatin, simvastatin and lovastatin.

Other features of the invention include those described above wherein the Agent is used at doses of 5 to 80 mg per day. When a dose range of 5 to 80 mg per day is referred to herein for the Agent other particular dosage ranges, which are further independent aspects of the invention, include (as appropriate) 10 to 80 mg per day, 10 to 60 mg per day, 10 to 40 mg per day, 5 to 40 mg per day, 5 to 20 mg per day, 10 to 20 mg per day, 20 to 60 mg per day, 20 to 40 mg per day and 40 to 60 mg per day. Particular dosages are 5, 10, 20, 40 and 80 mg per day. A particularly suitable starting dose of the Agent in the methods referred herein is 5 to 10 mg per day, especially 10 mg per day.

P450 3A4 substrates include; acetominophen, aldrin, aflentanil, amiodorane, astemizole, benzphetamine, budenoside, carbamazepine, cyclophosphamide, cyclosporin, dapsone, digitoxin, ditiazem, diazepam, erthromycin, etoposide, flutamide, hydroxyarginine, ifosphamide, imipramine, lansoprazole, lidocaine, lovatidine, losartan, lovastatin, midrazolam, nifedipine, omeprazole, quinidine, rapamycin, retenoic acid, steroids, tacrolimus, teniposide, theophyline, toremifene, triazolam, troleandomycin, verapamil, warfarin, zatosetron and zonisamide.

P450 3A4 inhibitors include; clotrimazole, ethinylestradiol, gestodene, itraconazole, ketoconazole, miconazole, diltiazem, naringenin, erthromycin, cyclosporin and triacetyloleandomycin.

P450 3A4 inducers include; carbamazepine, dexamethasone, phenobarbital, phenytoin, rifampin, sulfadimidine, sulfinipyrazone and triacetyloleandomycin.

Examples of other P450 inducers, inhibitors or substrates include those mentioned in Drug Metabolism Reviews (1997) Vol 29, Issue 1+2, pages 413–580, Rendic, S. and Di Carlo, F. J. "Human cytochrome P450 enzymes,: A status report summarising their reactions, substrates, inducers and inhibitors".

Dosages of the Agent may be administered according to the cholesterol lowering effect desired from a range of 5 to 80 mg per day in any number of unit dosages. Dosages of the drug which is an inducer, inhibitor or substrate of P450 3A4 are those which are advised for each drug, or which are commercially available. Advantageously, due to the lack of interaction at the level of P450 3A4, the skilled person may dose the Agent with a drug which is an inducer, inhibitor or substrate of P450 3A4 with out needing to make any adjustments.

The dose ranges and dosages described above are further independent features of the invention.

Preferably the Agent is bis[(E)-7-[4-(4-fluorophenyl)-6-isopropyl-2-[methyl(methylsulfonyl)amino]pyrimidin-5-yl](3R,5 S)-3,5-dihydroxyhept-6-enoic acid] calcium salt (illustrated in FIG. 1).

EXPERIMENTAL

The experiment below is used to determine the in vitro metabolic fate of [$^{14}$C]-labelled Agent in human hepatocytes and, in addition, to determine the specific P450 isozymes involved in [$^{14}$C]-labelled Agent metabolism, if any. The latter experiment involves an investigation of the effects of P450 selective chemical inhibitors (see Table 1) on the metabolism of [$^{14}$C] -labelled Agent.
COMPOUND: [$^{14}$C]-labelled Agent.

Chemical name: Bis[(E)-7-[4-(4-fluorophenyl)-6-isopropyl-2-[methyl(methylsulfonyl)amino]pyrimidin-5-yl](3R, 5S)-3,5-dihydroxyhept-6-enoic acid] calcium salt
Isomer: 3R,5S,6E Stereoisomer
Molecular weight: 1001.16 (Ca salt)
Formulation ingredients: The labelled Agent is dissolved in water to produce a solution suitable for addition to the incubates.
TISSUE SOURCE Human liver, suitable for the preparation of microsomes and hepatocytes, obtained from The International Institute for the Advancement of Medicine (Exton, USA). Human hepatocytes may, in addition, be obtained from Biowhittaker Ltd. or United Kingdom Human Tissue Bank (Leicester, England).

EXPERIMENTAL PROCEDURES (1) Metabolism of [$^{14}$C]-Labelled Agent by Human Hepatocytes

[$^{14}$C]-labelled Agent (1 µM or higher concentration if required for analytical sensitivity) was incubated with hepatocytes in culture obtained from two human organ donors. Cultures were terminated with ethanol after 0, 6, 24 and 48 hours of incubation and stored at approximately −20° C. until analysed. The metabolic competence of the hepatocytes was confirmed at the time of incubation by examining their ability to metabolise [$^{14}$C]-ethoxycoumarin (25 µM); aliquots were removed into methanol at the same time points as for the test compound.

Following incubation of [$^{14}$C]-ZD4522 with hepatocytes, metabolite profiles were generated by High Performance Liquid Chromatography (HPLC). The ability of hepatocytes to metabolise [$^{14}$C]-ethoxycoumarin was confirmed by HPLC.

Assessment of Data

Data generated was assessed with regard to the following:—

(1) Assess whether human hepatocytes metabolise [$^{14}$C]-labelled Agent.

(2) Quantitate the amount of each metabolite formed.

(2) Enzymes Involved in Metabolism of the Agent

[$^{14}$C]-labelled Agent (at an appropriate concentration) was incubated with human hepatic microsomes in the absence and presence of selective P450 inhibitors (see Table 1). Similar incubations of [$^{14}$C]-labelled Agent with individual heterologously expressed P450 isoenzymes was also performed. Incubations were terminated by the addition of an appropriate organic solvent. Metabolite profiles of the incubates are generated by HPLC.

TABLE 1

Selective chemical inhibitors of P450 isozymes

| P450 isozyme | Selective inhibitor |
|---|---|
| 1A2 | Furafylline |
| 2C9 | Sulphaphenazole |
| 2C19 | Omeprazole |
| 2D6 | Quinidine |
| 3A4 | Ketoconazole |

Assessment of Data

Data generated during this study was assessed with regard to the following:—

(a) The rate and extent of metabolism of [$^{14}$C]-labelled Agent.

(b) The ability of the selective P450 inhibitors to decrease the metabolism of [$^{14}$C]-labelled Agent was compared in order to determine the isozyme(s) involved in the metabolism of [$^{14}$C]-labelled Agent.

The ability of individual expressed P450 isoforms to metabolise [$^{14}$C]-labelled Agent was assessed to aid determination of the P450 isozyme(s) involved in the metabolism of [$^{14}$C]-labelled Agent.

c) These in vitro data can be used to predict the variability of the pharmacokinetics of the Agent in the population and the likely effects on the pharmacokinetics of the Agent during co-administration with known P450 enzyme inhibitors/inducers.

It was found that the Agent was not significantly metabolised by whole hepatocytes and that his was inhibited by sulphaphenazole and omeprazole.

For Treating Hyperlipidaemia and Associated Conditions in Post Transplant Patients Receiving Immunosuppressive Therapy.

Two common drugs used in suppressing the human immune system, cyclosporin and tacrolimus (formerly called FK506), are known to be metabolised by cytochrome P450 3A4. In particular cyclosporin is also a known inhibitor of P450 3A4 and is therefore likely to reduce the metabolism of any other drug which is metabolised by P450 3A4.

Therefore where immunosuppressive therapy is prescribed, such as with the drugs cyclosporin and tacrolimus (especially cyclosporin), the attendant physician must be cautious as to any other therapy which may be jointly presented to the patient in combination. Immunosuppressive therapy is most commonly used before, during and after human transplant operations. In particular with cardiac transplants the attendant physician may wish to also, place the patient on statin drug therapy to reduce future incidents of coronary heart disease, stroke, peripheral arterial occlusive disease or peripheral vascular disease, particularly in patients with elevated cholesterol or in normolipidaemic patients with other risk factors associated with heart disease. In particular within this special patient group (human transplant patients), the patients are at high risk of developing accelerated atherosclerosis in the transplant organ in an aggressive fashion and within a short period of time due, in part, to the surgical damage to the blood vessels during transplantation, any previously underlying untreated conditions and the immunosupressive therapy. Hyperlipidaemia is common after transplantation even in patients who did not suffer hyperlipidaemia prior to transplantation, incidence 60–80% of recipients.

It is known that certain immunosuppresive drugs, such as steroids, cyclosporin and tacrolimus, raise cholesterol levels in patients (Wierzbicki A S (1999) IJCP 53 (1) 54–59). In addition cyclosporin and tacrolimus may raise the levels of fibrinogen and lipoprotein (a) in the patient, further accelerating the progression of atherosclerosis in the transplant patient (Hohaye H, Clin. Transplant (1997) 11, 225–230 and Hilbrands L B, J. Am. Soc. Nephrol (1995) 5, 2073–2081). This unusually accelerated atherosclerosis is present in about 20% of heart transplant patients at 1 year and 40–65% at 5 years (Chang G. Et al. American Heart Journal (1998), 136(2), 329–334). The incidence of accelerated atherosclerosis has been reported as causing a 1–18% incidence of CHD at one year and 20–50% incidence of CHD at 3 years in cardiac transplant patients (Erdoes L S, J. Vasc. Surg. (1995) 22, 434–440). Lovastatin, pravastatin and simvastatin have all shown to lower cholesterol levels in heart transplant patients. In a placebo controlled study pravastatin increased survival of transplant patients by 1 year and significantly reduced the incidence of haemodynamic organ rejection. Because of the lower incidence of serious drug interaction with the immunosuppresive therapy pravastatin is currently the statin drug of choice in post transplant treatment regimes. However, as discussed above, pravastatin does not lower lipid/cholesterol levels to such a great extent as, for example, atorvastatin.

We have discovered that the Agent is extremely effective at treating hypercholesterolaemia in patients following transplantation and that the Agent is not metabolised by cytochrome P450 isoenzyme 3A4. Therefore we have found through the use of the Agent in a clinical study that the Agent may be conveniently dosed to patients who are undertaking immunosuppressive therapy without any clinically significant side effects associated with the concomitant dosing of the Agent and the immunosuppressive drug(s) and, in addition, also achieve much higher levels of cholesterol lowering than has previously been achieved, such as by the use of pravastatin.

We present as the first feature of the invention a method of providing safe non-interacting cholesterol lowering therapy to a human patient undertaking immunosuppressive chemotherapy which method comprises administering to the patient the Agent.

Particular patients undertaking immunosuppressive chemotherapy who may benefit from the method of the invention are those who:

1) suffer primary (type IIa) hypercholesterolaemia (LDL-L≧135 and TG<200);
2) suffer combined (type IIb) hypercholesterolaemia (LDL-C≧135 and TG≧200);
3) patients with established CHD or other atherosclerotic disease, such a PVD, stroke or peripheral arterial occlusive disease;
4) patients who are at high risk of developing CHD or other atherosclerotic disease, such as described above, because of a combination of risk factors. The term "high risk" is defined in the "Recommendations of Second Joint Task Force of European and other Societies on Coronary Prevention", (Wood, D. et. al. European Heart Journal, Atherosclerosis and Journal of Hypertension 1998) as absolute CHD risk of ≧20% over 10 years or will exceed 20% if projected to age 60 years. Whether a patient is at high risk or not may be determined by the charts which accompany the above recommendations and which charts are incorporated herein by reference. For example a male patient in his 40s who smokes and has a systolic blood pressure of 180 mm Hg or higher and a total plasma cholesterol concentration of 7 mmol/L or higher will be classified as high risk. Similarly other guidelines for reducing risk factors may be applied such as those described in;

a) JAMA, Jun. 16, 1993—Vol 629, No. 23, Pages 3015–3023—"Summary of the NCEP Adult Treatment Panel II Report"—specifically FIG. 1. Page 3018–3019 which is incorporated herein by reference.
b) Post Graduate Medical Journal 1993; 69(811): 359–369—"Management of hyperlipidaemia: guidelines of the British Hyperlipidaemic Association"—specifically Table V and Table VI which are incorporated herein by reference.
c) Heart 1998; 80 Supplement 2: S1–S29—"Joint British recommendations on prevention of coronary heart disease in clinical practice"—specifically FIG. 1 on pages S4–S5, which is incorporated herein by reference.

d) The Lancet 1995; December 2, Vol. 346, 1467–1471—"Sheffield risk and treatment table for cholesterol lowering for primary prevention of coronary heart disease"—specifically the Table appearing at page 1468, which is incorporated herein by reference.
5) patients who suffer type I or II diabetes;
6) patients who are about to or have already undertaken a heart transplant;

The statin therapy may be administered so as to achieve in the patient undertaking immunosuppressive chemotherapy.
1) A reduction in the internal thickness of coronary artery atheroma of $\geq 30\%$ as measured by IVUS.
2) A reduction of LDL-C of at least 30, 40, 50%.
3) A maintenance or increase of HDL-C of at least 5, 10, 15%.
4) A change in any of the above values better than pravastatin at a similar dose and over the same period.

As a further feature of the invention, and due also to the fact that the Agent is not metabolised to any significant extent by P450 isoenzymes, it is possible to administer, more safely than before, to a patient receiving immunosuppresive therapy a fibrate and the Agent. As discussed earlier the administration of a fibrate and a statin has previously been associated with a higher incidence of rhabdomyolysis and myopathy. In addition fibrate drugs do interact with cyclosporin due to both being metabolised by the same P450 isoenzyme. Therefore, the use of a statin and a fibrate drug in combination with immunosuppresive therapy was previously contraindicated due to the likelihood of possible serious interactions (Hunninghake 1992, Wanner C. Kidney Int. (1995) 52(suppl.), S60–S62; and Katznelson S. Contributions Nephrol. (1997) 120, 97–104). However, if possible, it would be advantageous to also administer a fibrate alongside a statin since fibrates are known to lower different lipoproteins than statins and therefore their combined pharmacology would be complementary in reducing even further the likelihood of CHD and other diseases mentioned above associated with the formation of atherosclerosis. Therefore the possibility of combining the Agent, which is not metabolised by P450 3A4, with a fibrate and an immunosuppresive therapy offers the additional possibility of lowering cholesterol to a greater extent in such patients than previously achieved and more safely than could previously be achieved by the administration of a statin, a fibrate and an immunosuppresive drug.

Fibrate drugs are thought to act through peroxisomal proliferating activator receptor-α (PPAR-α) and affect gene activation at a number of genes involved in atheroma. Patients on fibrate drugs show improved LDL subfraction distribution (reduced VLDL and raised HDL), reduced LDL and reduced triglyceride levels, and possible advantages through improving insulin sensitivity. Examples of fibrate drugs include, bezafibrate, ciprofibrate, fenofibrate and gemfibrozol.

By use of the term "safe non-interacting statin therapy" we mean that the Agent is not metabolised by P450 3A4 and therefore does not affect the metabolism of the immunosuppresive therapy or vice versa.

Diseases and conditions in which immunosuppressive therapy may be prescribed include, in addition to organ transplantation mentioned above, autoimmune diseases, including rheumatic disorders, such as, rheumatoid arthritis, osteoarthritis, lupus erthematosus; and other autoimmune disorders such as idiopathic thrombocytopenic purpura, autoimmune haemolytic anaemia and acute glomerulonephritis.

The agent may be administered at the same time as the immunosuppressive chemotherapy, or if not at the same time within a short time period of administration of the immunosuppressive therapy, such as in the same day, within 6, 3, 2 or 1 hour.

The Agent may be administered according to the cholesterol lowering effect desired from a range of 5–80 mg per day in any number of unit dosages, preferable once a day dosing. Ideal doses are 10, 20 and 40 mg once per day. Preferred doses are 20 and 40 mg once per day.

Particular immunosuppressive drugs which may be combined with the Agents are those which are metabolised by liver enzymes, such as by P450 3A4, and therefore are not likely to have a drug interaction with the Agent. Examples include those described above, cyclosporin and tacrolimus, as well as corticosteroids, which are also metabolised in the liver. Examples of corticosteroids include prednisone (especially used for organ transplantation). Preferably at least one of the immunosuppressive agents, if more than one agent is used, is either cyclosporin or tacrolimus, preferably cyclosporin.

EXAMPLE

The following non-limiting example is of a clinical trial to demonstrate the performance of this aspect of the invention.

Protocol

Title: A Double-blind, Parallel Group Study to Assess the Change in Coronary Artery Atheroma Burden Post Cardiac Transplantation as Measured via IVUS after 12 Months Dosing with the Agent versus Pravastatin Objectives: The primary objective of the study is to measure change in maximal mean intimal thickness of the anterior descending coronary artery as assessed by intravascular ultrasonography (IVUS) (read centrally) after 12 months of treatment with the Agent or pravastatin. A change from baseline of $\geq 30\%$ in intimal thickness is considered clinically significant.

The secondary objectives of the study are to measure the effects on coronary artery atheroma burden and to compare effects of the Agent with the following assessments:

evidence of organ rejection as assessed by adverse event reports.

measurement of LDL-C, HDL-C, apoB, apoA-I, Lp (a) concentrations, ex vivo platelet aggregation, fibrinogen, PAI-I, and the concentrations of circulating markers of vascular inflammation.

comparison of lipid values after 52 weeks of treatment.

measurement of inflammatory markers after 52 weeks of treatment (HLA antigen VCAM/ICAM expression as assessed by biopsy).

to determine the drug's safety and tolerability.

Type and number of subjects: Approximately 40 men and women (aged 18 years and older) post cardiac transplant with hypercholesterolemia and triglycerides<400 mg/dl at the time of randomization.

Trial treatment: Once daily doses of the Agent (10 mg) or pravastatin (10 mg) for two weeks, then titration of dose to 20 mg of the Agent or pravastatin 20 mg. After 4 weeks the dose should be titrated up to 40 mg of the Agent or 40 mg pravastatin. Patients who have had their dose titrated up to 40 mg may have their dose titrated down to 20 mg, at the discretion of the investigator.

Duration of treatment: Eligible subjects randomised to 1 of 2 treatment groups, the Agent or pravastatin, for 52 weeks.

Primary measure: Mean change from baseline in maximal mean intimal thickness, as assessed by IVUS (read centrally).

Secondary measures: Percent change from baseline in LDL-C at 6 and 12 months.

Percent change from baseline in total cholesterol (TC), low-density lipoprotein cholesterol (LDL-C), high-density lipoprotein cholesterol (HDL-C), LDL-C/HDL-C, TC/HDL-C, non-HDL-C/HDL-C, and triglycerides (TG).

Percent change from baseline in ApoB, ApoB/ApoA-1, ApoA-1, Lp (a), and particle subfractions at 6 and 12 months.

Percentage of subjects on each of the possible titrated doses at 12 months.

Endocardial rejection will be considered an adverse event.

Percent change from baseline in inflammatory markers (HLA antigen level and ICAM/VCAM expression).

Safety evaluation as determined by adverse events, physical examination, and laboratory data.

Trial Design

This is a multicenter, randomized, double-blind, parallel-group clinical trial. Within 1 to 4 weeks post surgery, subjects are randomized to receive either the Agent or pravastatin for 52 weeks. Subjects start treatment at a dose of 10 mg of either the Agent or pravastatin at Visit 2 and the dose is titrated to 20 mg at Visit 3 during the forced titration period. At Visit 4 and subsequent visits, the investigator has the option to increase each drug up to 40 mg during the optional titration period. Patients who have had their dose titrated up to 40 mg may have their dose titrated back down to 20 mg at the investigator's discretion.

(4) Subjects with a history of diabetic ketoacidosis within the past 5 years are excluded.

(5) uncontrolled hypothyroidism defined as a thyroid stimulating hormone (TSH)>1.5 times the ULN at Visit 2 or subjects whose thyroid replacement therapy was initiated within the last three months (6) use of concomitant medications as detailed below—except immune suppressants and diazepam (7) current alcohol and/or drug abuse (8) active liver disease or hepatic dysfunction as defined by elevations of $\geq 1.5$ times the ULN at Visit 2 in any of the following liver function tests: ALT, AST, or bilirubin (9) serum CK>3 times ULN at Visit 2

(10) serum creatinine>220 $\mu$mol/L (2.5 mg/dl)

(11) subjects with cancer or with a history of cancer who, in the opinion of the investigator, have more than a minimal chance of recurrence

(12) participation in another investigational drug trial less than 4 weeks before randomization into the trial

(13) subjects randomized to double-blind treatment who subsequently withdrew cannot re-enter this trial

(14) serious or unstable medical or psychological conditions that, in the opinion of the investigator, would compromise the subject's safety or successful participation in the trial

(15) subjects taking cyclic hormone replacement therapy (HRT), cyclic oral contraceptive therapy (OCT), a depot progesterone injection, or subjects whose non-cyclic HRT or OCT was initiated within the last 3 months

TRIAL DESIGN

|  | Pre-transplant | Forced Titration |  |  | Optional Titration |  |  |  |  |  |
|---|---|---|---|---|---|---|---|---|---|---|
| Visit | 1 | 2 | 3 | 4 | 5 | 6 | 7 | 8 | 9 | 10 | 11 |
| Week (W)/Month (M) |  | W0 | W2 | W4 | M2 | M3 | M4 | M5 | M6 | M9 | M12 |
| Agent (mg) |  | 10 | 20 | $\geq 20$* |  |  |  |  |  |  |  |
| PRAVASTATIN (mg) |  | 10 | 20 | $\geq 20$* |  |  |  |  |  |  |  |
|  | Randomisation** |  |  |  |  |  |  |  |  |  |  |

*Subjects who are tolerating 20 mg of the Agent or Pravastatin at Visit 4 may have their dose titrated up to 40 mg, at the discretion of the investigator.
**Subjects should be randomized within 4 weeks of cardiac transplantation and must not have received any other lipid lowering therapy post-surgery.

Inclusion Criteria (1) have undergone cardiac transplantation up to four weeks prior to randomization (2) fasting TG concentrations of <4.52 mmol/L (400 mg/dl)

Exclusion Criteria

Any of the following is regarded as a criterion for exclusion from the trial:

(1) Use of other cholesterol lowering drugs or lipid lowering dietary supplements or food additives post-transplantation prior to entering the study (2) history of serious or hypersensitivity reactions to other HMG-CoA reductase inhibitors (3) pregnant women, women who are breast feeding, and women of child bearing potential who are not using chemical or mechanical contraception or have positive serum pregnancy test (a serum β-Human chorionic gonadotropin [β-HCG] analysis)

DISALLOWED MEDICATIONS

| CLASS OF DRUG | GENERIC NAME |
|---|---|
| Antibiotics/antifungals | Erythromycin Base |
|  | Erythromycin Ethyl Succinate, Acetyl Sulfisoxazole |
|  | Rifampicin |
|  | Fluconazole |
|  | Ketaconazole |
|  | Itraconzole |
| Anti-epileptics/antidepressants | Phenytoin |
|  | Phenobarbitol |
|  | Fluoxetine |
|  | Carbemazepine |
| Acne treatment | Isotretinoin |
| Antiulcer drugs | Cimetidine |
|  | Cisapride |

-continued

DISALLOWED MEDICATIONS

| CLASS OF DRUG | GENERIC NAME |
|---|---|
| Systemic Steroids | Triamcinolone Acetonide |
| | Triamcinolone Diacetate |
| | Betamethasone |
| | Sodium Phosphate |
| | Betamethasone Acetate |
| | Hydrocortisone |
| | Hydrocortisone Acetate |
| | Hydrocortisone Sodium Phosphate |
| | Hydrocortisone Sodium Succinate |
| | Cortisone Acetate |
| | Dexamethasone |
| | Dexamethasone Acetate |
| | Dexamethasone Sodium |
| | Prednisone |
| | Methylprednisolone |
| | Methylprenisolone Acetate |
| | Methylprednisolone Sodium Succinate |
| | Prednisolone Tebutate |
| | Prednisolone Sodium Phosphate |
| | Methyltestosterone |
| | Fluoxymesterone |
| Antihistamine | Astemizole |
| | Terfenadine |
| Lipid Regulation | Niacin/Nicotinic Acid |
| | Probucol |
| | Psyllium Preparations |
| | Clofibrate |
| | Cholestyramine |
| | Colestipol Hydrochloride |
| | Gemfibrozil |
| | Atorvastatin |
| | Lovastatin |
| | Pravastatin (except study medication) |
| | Simvastatin |
| | Fluvastatin |
| | Cerevestatin |
| | Fish oils (any dose) |
| | lipid lowering dietary supplements |
| | lipid lowering food additives |
| Hormone Therapy | Estrogen and progesterone combinations which are bi or tri phasic. |

Friedewald Equation

The LDL-C level is calculated from the Friedewald equation as follows:

For SI Units (mmol/l)

$$LDL\text{-}C = \text{Total cholesterol} - [HDL\text{-}C + \text{Triglycerides}/2.2]$$

For non-SI Units (mg/dl):

$$LDL\text{-}C = \text{Total cholesterol} - [HDL\text{-}C + \text{triglycerides}/5]$$

Summary of NCEP Goals for Lipid Management[a]

| NCEP Risk Category | Target LDL-C (NCEP) |
|---|---|
| No CHD/PVD and 1 or no risk factors | <160 mg/dL |
| No CHD/PVD and 2 or more risk factors | <130 mg/dL |
| Clinically evident CHD/PVD | ≦100 mg/dL |

[a]Second Report of the Expert Panel on Detection, Evaluation, and Treatment of High Blood Cholesterol in Adults. Bethesda (MD): National Institutes of Health, National Heart and Lung Institute September 1993 Report No.: 93-3095.
NCEP National Cholesterol Education Program.

[a] Second Report of the Expert Panel on Detection, Evaluation, and Treatment of High Blood Cholesterol in Adults. Bethesda (MD): National Institutes of Health, National Heart and Lung Institute 1993 September Report No.: 93-3095.

NCEP National Cholesterol Education Program.

For Treating Hyperlipidaemia, and Associated Conditions, Using a Combination of the Agent and a Fibrate Drug or Niacin Myopathy and rhabdomyolysis have been associated with taking a statin in combination with gemfibrozil, niacin, cyclosporin or erythromycin, (HMG CoA reductase inhibitors, Hunninghake, Current Opinion in Lipidology (1992) 3, 22–28) which are all substrates for P450 3A4. Additionally, adverse events associated with taking a fibrate drug have also been reported to increase with concomitant statin therapy, such as a myosistis-flu like syndrome, which occasionally occurs in patients receiving gemfibrozil, increases to 5% of patients when a statin is also administered.

Combination of a statin with a fibrate drug is contraindicated on the labels, both in the USA and Europe, of all commercially available statins. Despite the possibility of the occurrence of serious drug interactions doctors do prescribe combination therapy of a statin and a fibrate drug to patients with more severe levels of hypercholesterolaemia, such as in patients with familial combined hyperlipidaemia, where the risk of a serious drug interaction is outweighed by the benefits of the combination therapy. It is recommended that where combination therapy of a fibrate drug and a statin is prescribed that patients should have their CK value determined on a regular-basis, typically every 6-weeks, until a stable pattern is established. Therapy is stopped if muscle symptoms occur in association with elevated CK activity. However, as quoted from the US label of Lipitor™ "there is no assurance that such monitoring [of CK levels] will prevent the occurrence of severe myopathy".

We have discovered that the Agent is extremely effective at treating mixed hyperlipidaemia and hypertriglyceridaemia in patients when combined with a fibrate drug and that the Agent is not metabolised by cytochrome P450 isoenzyme 3A4. Therefore we have found through the use of the Agent in a clinical study that the Agent may be conveniently dosed to patients who are also taking a fibrate drug without any clinically significant side effects associated with the concomitant dosing of the Agent and the fibrate drug. In addition much higher levels of lipid lowering than has previously been achieved can be achieved by the use of the Agent and a fibrate drug. The combination is of most use in mixed hyperlipidemia where the LDL and VLDL and TGs are all elevated.

We present as the first feature of the invention a method of providing safe non-interacting lipid lowering combination therapy to a mammal, including a human patient, preferably a patient suffering mixed hyperlipidaemia and hypertriglyceridaemia, which method comprises administering to the patient the Agent and a fibrate drug or niacin.

By the term "combination" as used herein we mean either (1) that the Agent and the fibrate drug of the combination are administered together in the same pharmaceutical formulation or (2) that the Agent and the drug are administered separately. When administered separately components of the combination may be administered to the patient simultaneously or sequentially.

By the term "fibrate drug" we mean the class of drugs which are based around the structure/activity of fibric acid and such drugs include the following commercially available versions; bezafibrate, clofibrate, ciprofibrate, fenofibrate and gemfibrizol, preferably fenofibrate.

Preferred patients in which the combination of the invention is to be administered are those who have already been found to suffer from myopathy or rhabdomylosis when treated with a statin and/or with a fibrate drug which is metabolised by P450 3A4.

Particular patients who may benefit from the method of the invention are those who:
1) suffer combined (type IIb) hypercholesterolaemia (typically LDL-C≧135 mg/dL and TG≧200 mg/dL);
2) suffer familial (type IV and V) hypercholesterolaemia;
3) patients suffering secondary hypercholesterolaemia from such conditions as:
   a) diabetes (type I or II),
   b) nephrotic syndrome,
   c) uremia,
   d) hyperthyroidism, and
   e) obstructive liver disease.
4) patients with established CHD or other atherosclerotic disease, such a PVD, stroke or peripheral arterial occlusive disease;
5) patients who are at high risk of developing CHD or other atherosclerotic disease, such as described above, because of a combination of risk factors. The term "high risk" is defined in the "Recommendations of Second Joint Task Force of European and other Societies on Coronary Prevention", (Wood, D. et. al. European Heart Journal, Atherosclerosis and Journal of Hypertension 1998) as absolute CHD risk of ≧20% over 10 years or will exceed 20% if projected to age 60 years. Whether a patient is at high risk or not may be determined by the charts which accompany the above recommendations and which charts are incorporated herein by reference. For example a male patient in his 40s who smokes and has a systolic blood pressure of 180 mm Hg or higher and a total plasma cholesterol concentration of 7 mmol/L or higher will be classified as high risk. Similarly other guidelines for reducing risk factors may be applied such as those described in;
   a) JAMA, Jun. 16, 1993—Vol 629, No. 23, Pages 3015–3023—"Summary of the NCEP Adult Treatment Panel II Report"—specifically FIG. 1. Page 3018–3019, which is incorporated herein by reference.
   b) Post Graduate Medical Journal 1993; 69(811): 359–369—"Management of hyperlipidaemia: guidelines of the British Hyperlipidaemic Association"—specifically Table V and Table VI, which are incorporated herein by reference.
   c) Heart 1998; 80 Supplement 2: S1–S29—"Joint British recommendations on prevention of coronary heart disease in clinical practice"—specifically FIG. 1 on pages S4–S5, which is incorporated herein by reference.
   d) The Lancet 1995; December 2, Vol. 346, 1467–1471—"Sheffield risk and treatment table for cholesterol lowering for primary prevention of coronary heart disease"—specifically the Table appearing at page 1468, which is incorporated herein by reference.

The statin therapy may be administered so as to achieve in the patient receiving a fibrate drug or niacin:
1) a reduction of LDL-C of at least 30, 40, 50, 60, 70 or 80%.
2) a maintenance or increase of HDL-C of at least 5, 10, 15%.
3) a reduction in triglycerides of at least 10, 20, 30 or 40%.

The combination of the fibrate, or niacin, and the Agent may be applied as separate dosage forms, which may be taken simultaneously or sequentially, or in a combined dosage form. The combination of the fibrate and the Agent will also have an additive or synergistic effect on the reduction in LDL-C, maintenance or increase of HDL-C or reduction in triglyceride in the patients blood.

In addition the combination of niacin and the Agent may be applied as separate dosage forms, which may be taken simultaneously or sequentially, or in a combined dosage form. The combination of the fibrate and the Agent will also have an additive or synergistic effect on the reduction in LDL-C, maintenance or increase of HDL-C or reduction in triglyceride in the patients blood.

Doses of the Agent which are administered are at the discretion of the attendant physician generally taking into account the severity of the disease, the age, weight and sex of the patient. However typical doses will be from 5 to 80 mg per day orally, preferably as a once a day oral tablet form.

Doses of the fibrate drug or niacin which are administered in the combination of the invention also are at the discretion of the attendant physician taking into account all of the above factors plus in particular which drug is used.

For clofibrate (such as Atromid-S®) 20–30 mg/kg body weight daily in 2 or 3 divided oral doses after meals is typical.

For bezofibrate (such as Bezalip®) 400 mg once a day orally, after food at night or in the morning, is typical.

For fenofibrate (such as Lipantil®) 200 mg once a day, or 62 mg three times a day, with food is typical.

For gemfibrozil (such as Lopid®) 600 mg twice a day orally is typical.

For cipofibrate (such as Modalim®) 100 mg once a day orally is typical.

For niacin (NIASPAN®, an extended release niacin formulation, and preferred feature) 500 mg once to four times daily, preferably twice or four times daily.

A preferred fibrate drug is fenofibrate.

Preferably the AGENT is administered to a patient receiving niacin at 10 mg or 40 mg daily doses.

The particular aspect of this invention is illustrated by the following non-limiting examples:

Clinical Trial

A Randomised, Non-controlled, Single-centre, Open-label, 3-way Crossover Trial to Assess the Effect of Co-administration of the Agent and Fenofibrate on the Pharmacokinetics of Each Compound in Healthy Male Volunteers Objectives: The primary objective of this trial is to assess the effect of co-administration of the Agent and fenofibrate on the pharmacokinetics of both the Agent and fenofibrate The safety of all volunteers will be ensured by clinical monitoring Type and number of volunteers: 14 healthy male volunteers Trial design: The trial will be a randomised, non-controlled, 3-way crossover study carried out at a single centre Trial treatment: This trial will consist of three 7-day treatment periods (Periods A, B, and C). Volunteers will receive, in random order, a 10 mg capsule of the Agent once daily for 7 days, a 67 mg fenofibrate capsule 3 times daily for 7 days and the combination for 7 days.

There will be a minimum of a 3-week washout between each trial period.

Duration of treatment: The study will consist of 3 periods of 7-day dosing (a total of 21 dosing days) with a 3-week washout between dosing in Periods A, B and C.

Primary endpoints: The primary endpoints are:
AUC(0–24) and $C_{max}$ of the Agent in the presence and absence of fenofibrate
AUC(0–8) and $C_{max}$ of fenofibrate in the presence and absence of the Agent Secondary endpoints: the secondary endpoints are:
$t_{max}$, $t_{1/2}$, $C_{min}$ for the Agent in the presence and absence of fenofibrate
$t_{max}$, $t_{1/2}$, $C_{min}$ for fenofibrate in the presence and absence of the Agent
safety assessments: symptoms, blood pressure and pulse rate, ECG, clinical chemistry, haematology and urinalysis

TRIAL PLAN
Summary of procedures - overall plan for Trial Periods A, B and C

| Trial Days | Medical | Doses of the Agent/ fenofibrate or combination | P & BP | 12 lead ECG | Safety Blood & Urine | Kinetics of the Agent | Kinetics Fenofibrate |
|---|---|---|---|---|---|---|---|
| Pre-trial | + |   | + | + | +[a] |   |   |
| −1 |   |   |   |   | +[b] |   |   |
| 1 |   | + |   |   |   | +[c] | +[c] |
| 2 |   | + |   |   | +[b] | +[d] | +[e] |
| 3 |   | + |   |   |   | +[d] | +[e] |
| 4 |   | + |   |   | +[b] |   |   |
| 5 |   | + |   |   |   |   |   |
| 6 |   | + |   |   | +[b] | +[d] | +[c] |
| 7 |   | + | + | + |   | +[d] | +[e] |
| 8 |   |   |   |   | +[b] | +[d] |   |
| 9 |   |   |   |   |   | +[d] |   |
| 10 |   |   |   |   | +[b] | +[d] |   |
| Post-trial | + |   | + | + | +[a] | +[d] |   |

[a]Full clinical chemistry, haematology and urine labstix.
[b]Clinical chemistry only: urea, creatinine, total protein, albumin, uric acid, total bilirubin (and unconjugated and conjugated bilirubin if total bilirubin raised), alkaline phosphatase, alanine aminotransferase (ALT), aspartate aminotranseferase (AST), gamma glutamyltransferase, creatine kinase (CK), sodium, potassium, calcium, cholesterol and triglycerides.
[c]Pre-dose all trial periods.
[d]Only trial periods when volunteers receive the Agent
[e]only trial periods when volunteers receive fenofibrate
P = pulse; BP = blood pressure

TRIAL PLAN II
Trial Day 7 in Periods A, B and C

| Time | P & BP (L) | 12 lead ECG | Safety blood & urine[e] | Kinetics of the Agent[b] | Kinetics fenofibrate[c] | Meals & Fluids |
|---|---|---|---|---|---|---|
| Pre-dose | + | + |   | + | + | B |
| Dose (0 h) |   |   |   |   |   | D |
| 0.5 h |   |   |   | + | + |   |
| 1 h |   |   |   | + | + |   |
| 2 h |   |   |   | + | + | D |
| 3 h | + | + |   | + | + |   |
| 4 h |   |   |   | + | + | M, F |
| 5 h | + | + |   | + | + |   |
| 6 h |   |   |   | + | + |   |
| 8 h |   |   |   | + | + | S |
| 10 h |   |   |   | + |   | M |
| 12 h | + | + |   | + | + | F |
| 14 h |   |   |   |   |   | S |
| 18 h |   |   |   | + |   | W |
| 24 h | + | + | +[a] | + |   |   |
| 30 h |   |   |   | + |   |   |
| 48 h |   |   |   | + |   |   |
| 54 h |   |   |   | + |   |   |
| 72 h |   |   | +[a] | + |   |   |

[a]clinical chemistry only: urea, creatinine, total protein, albumin, uric acid, total bilirubin (and unconjugated and conjugated bilirubin if total bilirubin raised), alkaline phosphatase, ALT, AST, gamma glutamyltransferase, CK, sodium, potassium, calcium, cholesterol and triglycerides.
[b]Only trial periods when volunteers receive the Agent
[c]Only trial periods when volunteers receive fenofibrate
L = lying; P = pulse; BP = blood pressure; D = drink; S = snack; M = meal; F = free access to permitted fluid and food; W = free access to water only

1 OBJECTIVES

Primary Objective

The primary objective of this trial is to assess the effect of co-administration of the Agent and fenofibrate on the pharmacokinetics of both the Agent and fenofibrate.

Secondary Objective

There is no secondary objective for this trial.

The safety of all volunteers will be ensured by clinical monitoring.

Design

The trial will be a randomised, non-controlled, open-label, 3-way crossover study carried out at a single centre.

Volunteers will receive 3 treatment regimens in random order:

10 mg of the Agent once daily for 7 days
fenofibrate (Lipantil™) 67 mg×3 daily for 7 days
the Agent (10 mg once daily) and fenofibrate (Lipantil™, 67 mg×3 daily) given in combination for 7 days There will be a minimum of 3 weeks (21 days) washout between each treatment period.

Inclusion Criteria

For inclusion in the trial, volunteers must meet all of the following criteria:
- male, aged between 18 and 65 years inclusive
- normal clinical examination, including medical history, resting electrocardiogram (ECG) and 24-hour continuous ambulatory ECG (if not performed in the past 12 months)
- negative screens for serum hepatitis B surface antigen and hepatitis C antibody and a normal screen for ferritin within the previous 12 months
- weight not differing by more than 20% from the desirable weight (Metropolitan Height and Weight Tables)

Exclusion Criteria

Volunteers must be excluded from the trial if any of the following criteria are met:
- use of any medication or therapy, including drugs of abuse
- receipt of another new chemical entity in the 4 months before dosing in this trial (a new chemical entity is defined as a compound which has not been submitted for marketing authorisation)
- participation in another trial within 3 months before the start of the present trial, apart from non-invasive methodology trials in which no drugs were given
- any acute illness within 2 weeks before the start of the trial
- any clinically significant abnormalities in clinical chemistry, haematology or urinalysis results. In addition the following clinical chemistry parameters should be no greater than the upper limit of normal: total bilirubin, ALT, AST and CK
- risk (in the investigator's opinion) of transmitting, through blood or other body fluids, the agents responsible for acquired immune deficiency syndrome (AIDS), hepatitis B or hepatitis C
- definite or suspected personal history or family history of adverse drug reactions, or hypersensitivity to drugs with a similar chemical structure to the Agent or related statins, or fenofibrate and related fibrate drugs
- history or presence of gastrointestinal, hepatic, biliary or renal disease or other condition known to interfere with absorption, distribution, metabolism or excretion of drugs
- history of Gilbert's syndrome
- if participation in the trial would result in the volunteer donating more than 1350 ml of blood in the 12 months before the end of the trial
- excessive intake of alcohol, defined as a maximum weekly intake of greater than 28 units (I unit equals half a pint of beer or a measure of spirits)
- treatment in the previous 3 months with any drug known to have a well-defined potential for hepatotoxicity (eg, halothane)
- clinical judgement by the investigator or the volunteer's general practitioner that the volunteer should not participate in the trial Volunteer Restrictions Volunteers will be required to:
- abstain from taking any medication (including over-the-counter remedies) from 96 hours before Trial Day 1 to 72 hours after receiving the last dose of the Agent or morning dose of fenofibrate in each trial period unless the investigator has given prior consent
- fast from midnight on the night before each trial day and eat a light breakfast on arrival on Trial Day 1 to 7 in each trial period
- refrain from driving, cycling, using machinery (drills, sanders, sharp instruments etc.) for 24 hours after receiving first dose on Trial Day 7 in each period
- remain for 24 hours after receiving first dose on Trial Day 7 in each trial period
- abstain from smoking, consuming grapefruit, grapefruit juice, liquorice or caffeine-containing drinks or foods (eg, coffee, tea, cocoa, chocolate and cola) from midnight before Trial Day 1 until 72 hours after receiving the last dose of the Agent or morning dose of fenofibrate in each trial period
- abstain from drinking alcohol from 96 hours before Trial Day 1 until 72 hours after receiving the last dose of the Agent or morning dose fenofibrate in each trial period
- refrain from physical exercise from 96 hours before Trial Day 1 until 72 hours after receiving the last of the Agent or morning dose of fenofibrate in each trial period
- refrain from potentially hazardous work or activities, from receiving the first dose of the Agent or fenofibrate until the post-trial medical
- abstain from donating blood during the trial and for 3 months following their last dose of trial treatment Formulation, Presentation and Storage Dosage and Administration Capsules of the Agent or fenofibrate will be taken orally with 200 ml of purified water with the volunteer sitting in an upright position.

On Trial Days 1 to 7 of each treatment period, volunteers will receive one of the following treatments:
- 1×10 mg capsule of the Agent to be taken between 08:30 and 09:30 hours
- 3×67 mg fenofibrate capsules
  - the 1st capsule to be taken between 08:30 and 09:30 hours
  - the $2^{nd}$ capsule to be taken between 16:30 and 17:30 hours with food
  - the $3^{rd}$ capsule to be taken between 22:30 and 23:30 hours with food
- 1×10 mg capsule of the Agent and 3×67 mg fenofibrate capsules:

1 capsule of the Agent and the 1st fenofibrate capsule to be taken simultaneously between 08:30 and 09:30 hours the 2nd fenofibrate capsule to be taken between 16:30 and 17:30 hours with food the 3rd fenofibrate capsule to be taken between 22:30 and 23:30 hours with food On Trial Days 1 to 6 of each trial period, volunteers will visit the unit daily and will be allowed to leave the unit immediately after administration of doses of the Agent, fenofibrate or the the Agent/fenofibrate combination, except on Trial Day 7 when volunteers will remain resident for 24 hours.

In trial periods when the volunteers are randomised to fenofibrate, they will take the further 2 doses of fenofibrate at home. The volunteers will be provided with 1 pot of fenofibrate to be taken as outlined above. Volunteers will be issued with a pre-set timer to ensure that the dose is taken at the correct time, and a diary card to document the dose was taken.

When the the Agent and fenofibrate are given to the volunteers, the tear-off labels will be attached to the appropriate case report form (CRF). The investigator must ensure that each volunteer receives the correct treatment.

Clinical and Laboratory Assessments

Primary Endpoints

The following parameters will be measured as primary endpoints:

AUC(0–24) and $C_{max}$ of the Agent in the presence and absence of fenofibrate

AUC(0–8) and $C_{max}$ of fenofibrate in the presence and absence of the Agent

Secondary Endpoints

The following parameters will be measured as secondary endpoints:

$t_{max}$, $t_{1/2}$, $C_{min}$ for the Agent in the presence and absence of fenofibrate $t_{max}$, $t_{1/2}$ and $C_{min}$ for fenofibrate in the presence and absence of the Agent safety assessments: symptoms, blood pressure and pulse rate, ECG, clinical chemistry, haematology and urinalysis.

Pharmaceutical Compositions

The following Example illustrates, but is not intended to limit, pharmaceutical dosage forms which are suitable for use in the invention as defined herein:

| Capsule | mg |
| --- | --- |
| The Agent | 5.0 |
| Lactose | 42.5 |
| Cornstarch | 20.0 |
| Microcrystalline cellulose | 32.0 |
| Pregelatinised starch | 3.3 |
| Hydrotalcite | 1.1 |
| magnesium stearate | 1.1 |

Capsules containing 1, 2.5 or 10 mg of the Agent may be obtained similarly using more or less lactose as appropriate, to maintain a total fill weight of 105 mg.

| ABBREVIATIONS AND CONVENTIONS USED | |
| --- | --- |
| Abbreviation | Term |
| ALT | alanine aminotransferase |
| ALP | alkaline phosphatase |
| apo B | apolipoprotein B 100 |
| AST | aspartate aminotransferase |
| AUC | area under the concentration curve from zero to infinity |
| AUC(0–t) | area under the curve of plasma concentration against time from zero to time of last quantifiable concentration |
| CABG | Coronary artery bypass graft |
| $C_{max}$ | maximum concentration |
| CK | creatinine kinase |
| CVA | cerebrovascular accident |
| ECG | electrocardiogram |
| EAS | European Atherosclerosis Society |
| EDTA | ethylenediamine-tetraacetic acid |
| XGT | Gemma glutaryl transferase |
| HMG-CoA | 3-hydroxy-3-methylglutaryl coenzyme A |
| HDL | high-density lipoprotein |
| HPLC | high-performance liquid chromatography |
| HRT | hormone replacement therapy |
| IU | International Units |
| IVUS | Intravascular ultrasenography |
| LDL | low density lipoprotein |
| LDL-C | low density lipoprotein cholesterol |
| MVA | mevalonic acid |
| NC | not calculable |
| NCEP | national cholesterol eduction program |
| NDSR | national data system for research |
| THC | tetrahydrocannabinol |
| TG | triglyceride |
| $t_{1/2}$ | terminal elimination half-life |
| $t_{max}$ | time of maximum concentration |
| TC | total cholesterol |
| TG | triglycerides |
| TIA | transient ischemic attack |
| TSH | thyroid stimulating hormone |
| ULN | upper limit of normal |
| VLDL | very low-density lipoprotein |

What is claimed is:

1. A non-interacting drug combination comprising a first drug, which is the HMG-CoA reductase inhibitor (E)-7-[4-(4-fluorophenyl)-6-isopropyl-2-[methyl(methylsulfonyl)amino]pyrimidin-5-yl](3R,5S)-3,5-dihydroxyhept-6-enoic acid or a pharmaceutically acceptable salt thereof, and a second drug, which is selected from the group consisting of bezafibrate, clofibrate, ciprofibrate, fenofibrate and niacin.

2. A non-interacting drug combination, as claimed in claim 1, wherein the second drug is fenofibrate.

3. A pharmaceutical formulation comprising the non-interacting drug combination of claim 1 together with a pharmaceutically-acceptable diluent, carrier or adjuvant.

4. A method for the treatment of hypercholesterolaemia or mixed hyperlipidaemia in a patient in need thereof, said method comprising administering to said patient an effective amount of the pharmaceutical formulation of claim 3.

\* \* \* \* \*

UNITED STATES PATENT AND TRADEMARK OFFICE
CERTIFICATE OF CORRECTION

| | | |
|---|---|---|
| PATENT NO. | : 6,982,157 B1 | Page 1 of 1 |
| APPLICATION NO. | : 09/889414 | |
| DATED | : January 3, 2006 | |
| INVENTOR(S) | : John S. Pears et al. | |

It is certified that error appears in the above-identified patent and that said Letters Patent is hereby corrected as shown below:

Field (75) Inventors: add --Yamaguchi, Yoshitaka (JP)--

Signed and Sealed this

Tenth Day of April, 2007

JON W. DUDAS
*Director of the United States Patent and Trademark Office*